(12) United States Patent
van der Plaats et al.

(10) Patent No.: US 7,811,808 B2
(45) Date of Patent: Oct. 12, 2010

(54) PORTABLE PRESERVATION APPARATUS FOR A DONOR ORGAN

(75) Inventors: Arjan van der Plaats, Groningen (NL); Gijsbertus Jacobus Verkerke, Glimmen (NL); Gerhard Rakhorst, Groningen (NL); Rutger Jan Ploeg, Haren (NL); Nils Arnaud 't Hart, Ureterp (NL); Hendrik Gerrit Derk Leuvelink, Vries (NL)

(73) Assignee: Organ Assist B.V., Groningen (NL)

( * ) Notice: Subject to any disclaimer, the term of this patent is extended or adjusted under 35 U.S.C. 154(b) by 406 days.

(21) Appl. No.: 10/566,415

(22) PCT Filed: Jul. 27, 2004

(86) PCT No.: PCT/NL2004/000539

§ 371 (c)(1),
(2), (4) Date: Jun. 22, 2006

(87) PCT Pub. No.: WO2005/009125

PCT Pub. Date: Feb. 3, 2005

(65) Prior Publication Data

US 2007/0184545 A1    Aug. 9, 2007

(30) Foreign Application Priority Data

Jul. 30, 2003 (NL) .................................. 1024022

(51) Int. Cl.
*A01N 1/00* (2006.01)
*A01N 1/02* (2006.01)

(52) U.S. Cl. .................................... 435/284.1; 435/1.2

(58) Field of Classification Search .............. 435/284.1, 435/1.2; *A01N 1/02*
See application file for complete search history.

(56) References Cited

U.S. PATENT DOCUMENTS 3,632,473 A    1/1972    Belzer et al.

(Continued)

FOREIGN PATENT DOCUMENTS

DE           37 12200 A1    10/1988

(Continued)

OTHER PUBLICATIONS

Yanaga K., Makowka L., Lebeau G., Hwang R.R., Shimada M., Kakizoe S., Demetris A.J., Starzl T.E., "A New Liver Perfusion and Preservation System for Transplantation Research in Large Animals", Journal of Investigative Surgery, 1990, vol. 3, pp. 65-75.

*Primary Examiner*—William H Beisner
*Assistant Examiner*—Danielle Henkel
(74) *Attorney, Agent, or Firm*—Pearne & Gordon LLP

(57) ABSTRACT

A portable preservation apparatus of the cold storage type for a donor organ, comprising a cooling box provided with an organ chamber for receiving a donor organ in preservative fluid and a lid, wherein, on the side which operatively faces the organ chamber, the lid is provided with a connector which is detachably connected to the lid, which connector is provided with passages for one or more connecting pieces connected with the donor organ and one or more pipes connected with at least one perfusion pump, wherein the at least one perfusion pump is a miniature pump mounted at least partly in the lid and wherein the apparatus further comprises at least one oxygenator, an oxygen container, one or more electronic modules and a power supply module.

10 Claims, 7 Drawing Sheets

U.S. PATENT DOCUMENTS

| | | | |
|---|---|---|---|
| 3,660,241 A | | 5/1972 | Michielsen |
| 3,877,843 A | | 4/1975 | Fischel |
| 3,914,954 A | | 10/1975 | Doerig |
| 3,995,444 A | | 12/1976 | Clark et al. |
| 4,242,883 A | | 1/1981 | Toledo-Pereyra |
| 4,745,759 A | | 5/1988 | Bauer et al. |
| 5,051,352 A | | 9/1991 | Martindale et al. |
| 5,285,657 A | | 2/1994 | Bacchi et al. |
| 5,326,706 A | | 7/1994 | Yland et al. |
| 5,356,771 A | | 10/1994 | O'Dell |
| 5,385,821 A | * | 1/1995 | O'Dell et al. .................. 435/1.2 |
| 5,476,763 A | * | 12/1995 | Bacchi et al. ............. 435/284.1 |
| 5,494,822 A | | 2/1996 | Sadri |
| 5,586,438 A | * | 12/1996 | Fahy ............................. 62/78 |
| 5,681,740 A | * | 10/1997 | Messier et al. ............ 435/284.1 |
| 5,965,433 A | * | 10/1999 | Gardetto et al. ........... 435/284.1 |
| 6,046,046 A | * | 4/2000 | Hassanein ................ 435/284.1 |
| 6,100,082 A | | 8/2000 | Hassanein |
| 6,673,594 B1 | * | 1/2004 | Owen et al. .............. 435/284.1 |
| 2002/0012988 A1 | | 1/2002 | Brasile |
| 2003/0054540 A1 | * | 3/2003 | Alford et al. ............. 435/284.1 |

FOREIGN PATENT DOCUMENTS

| | | |
|---|---|---|
| DE | 199 28 485 C1 | 10/2000 |
| EP | 0 347 923 A1 | 12/1989 |
| EP | 0 553 401 A1 | 8/1993 |
| WO | WO 84/00493 | 2/1984 |
| WO | WO 88/05261 | 7/1988 |
| WO | WO 99/15011 | 4/1999 |
| WO | WO 00/60936 | 10/2000 |
| WO | WO 01/33959 A2 | 5/2001 |
| WO | WO 02/26034 A2 | 4/2002 |
| WO | WO 03/024214 A1 | 3/2003 |

* cited by examiner

PORTABLE PRESERVATION APPARATUS FOR A DONOR ORGAN

The invention relates to a portable preservation apparatus for a donor organ, comprising a cooling box provided with an organ chamber for receiving a donor organ in preservative fluid and a lid.

The invention is particularly but not exclusively suitable for preservation of a donor liver or a donor kidney. The following will focus on use for a donor liver. For other organs, an adjustment to the specific structure of these organs is needed.

The transplantation procedure of a liver comprises three stages, viz. 1) the donor operation, 2) the organ preservation and the transport and 3) the implantation in the recipient. The donor operation consists of cannulating the arteria hepatica (HA) and the portal vein (PV), via which the liver is then washed with the aid of a cold (4° C.) fluid, such as for instance the University of Wisconsin preservation (UW fluid). After washing, the cold UW fluid remains in the liver and the liver is packaged in a plastic bag filled with extra UW fluid and tied up. Around this, a second bag is provided which has been filled with cold physiological salt and then a third bag for extra strength and sterility. This whole is then placed in a portable cooling box which has been filled with melting ice and is then closed. This manner of preservation is called the 'static cold storage' (CS) and is the current standard method for liver preservation. After maximally approx 12 hours, the liver is to be implanted in the receiving patient. This is done by connecting the blood vessels of the donor liver with the vessels of the recipient and then washing the donor liver clean with a special fluid or the blood of the patient. After this, complete reperfusion of the liver takes place.

Drawbacks of this procedure are that the period of time of 12 hours is not very long, and that intermediate analysis of the viability and the condition which the liver is in is not possible.

The invention contemplates providing an improved preservation apparatus which is based on the known cold storage method, but reduces the drawbacks associated therewith. For this purpose, according to the invention, a portable preservation apparatus of the above-described type is characterized in that, on the side which operatively faces the organ chamber, the lid is provided with a connector detachably connected to the lid, which connector is provided with passages for one or more connecting pieces connected with the donor organ and one or more pipes connected with at least one perfusion pump, where the at least one perfusion pump is a miniature pump mounted at least partly in the lid and where the apparatus further comprises at least one oxygenator, an oxygen container, one or more electronic modules and a power supply module.

An advantage of the apparatus according to the invention is that the actions to be performed by the surgeon who performs the donor operation conveniently fit the already established CS routine, so that the risk of errors is small. Also, the apparatus according to the invention can be designed as a really portable apparatus, which simplifies the practical application of the apparatus. It is further possible to intermediately take samples to determine the quality of the donor organ present in the apparatus according to the invention.

It is noted that research concerning kidney transplantations has shown that, when a kidney is continuously perfused by means of a pump system during the cold preservation stage, the preservation period can be considerably extended. Continuous perfusion also makes it possible to take intermediate samples of the fluid and to monitor perfusion characteristics. It has further been found that the quality of continuously perfused kidneys is considerably better than that of statically stored kidneys, so that it appears possible to use kidneys of poorer quality for transplantation as well, such as for instance kidneys of donors who had a cardiac arrest. This would considerably increase the 'donor pool'.

A preservation apparatus provided with a pump system for continuous perfusion of kidneys or livers is described in WO 0133959. The pump system used in this known apparatus comprises a compressed air-driven membrane pump apparatus, which comprises a first fluid tank with supply and discharge pipes and which, in turn, has been placed in a second fluid tank. The second fluid tank is located below the reception space for an organ to be preserved. The membrane pump apparatus is arranged such that compressed air used for the drive is also utilized to aerate the fluid in the second fluid tank. Although this known preservation apparatus has a relatively simple construction, it is fairly sizeable and therefore difficult to transport.

Further, from U.S. Pat. Nos. 6,046,046 and 6,100,082, a perfusion apparatus is known for preserving a donor organ in functioning condition during a preservation period. For this purpose, the donor organ is placed in a container filled with a preservative fluid, while, further, via one or more main arteries and/or veins, preservative fluid is passed through the organ. This known apparatus is also fairly sizeable and has been mounted in a mobile cart. The known apparatus is not portable. Also, in the known apparatus, the donor organ is not cooled. Further, the known apparatus has in the first instance been designed for preserving a donor heart, but in U.S. Pat. No. 6,046,046, applications for other organs, such as kidneys and livers, are also mentioned. Also, the use of this known apparatus demands relatively much adaptation of the surgical team, which stands in the way of an application on a larger scale.

In the following, the invention will be further described with reference to the appended drawing of an exemplary embodiment, in which:

FIG. 1 diagrammatically shows, in perspective view, an example of a portable preservation apparatus according to the invention in closed condition;

Figure 1:
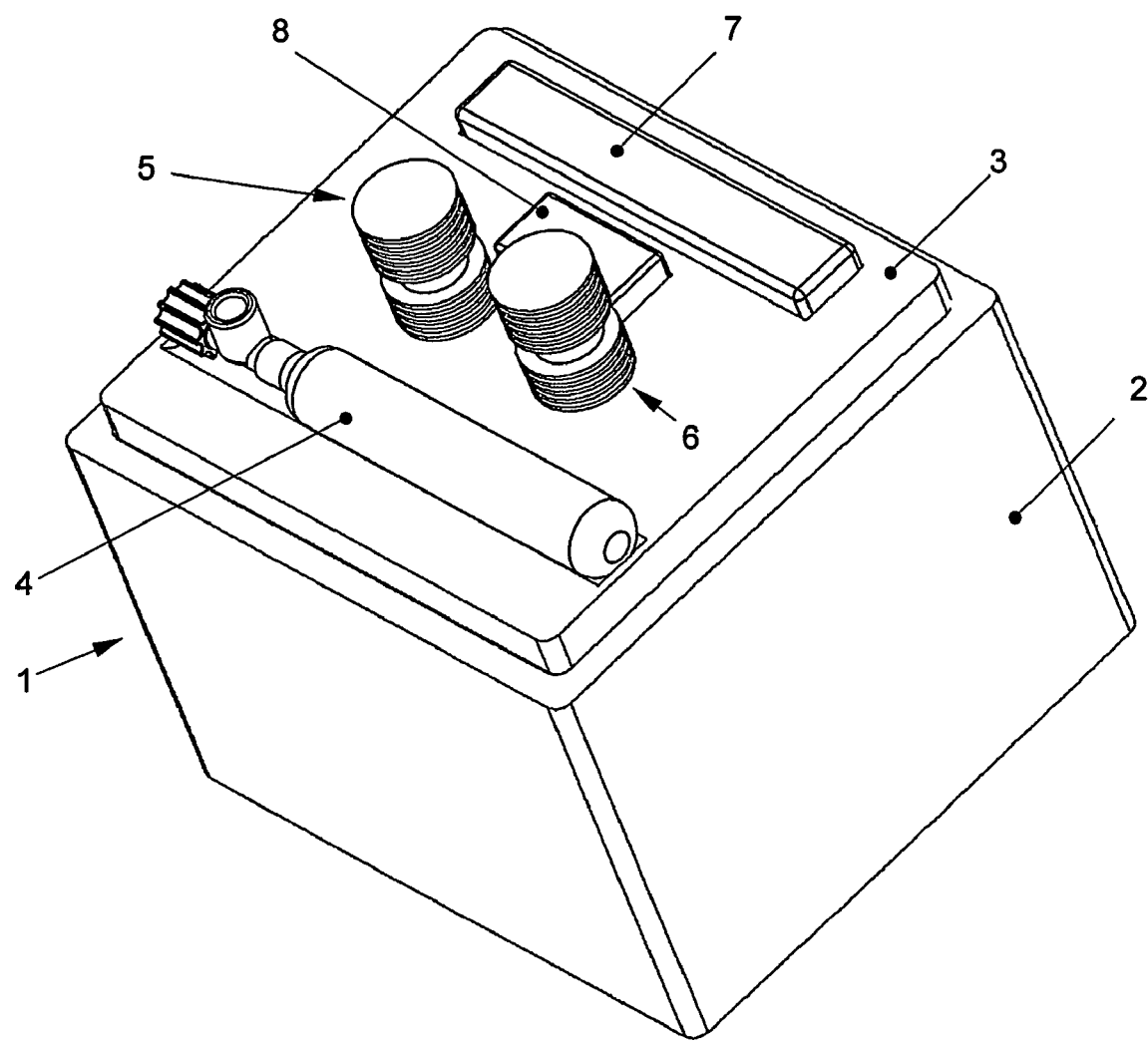
Figure 4:
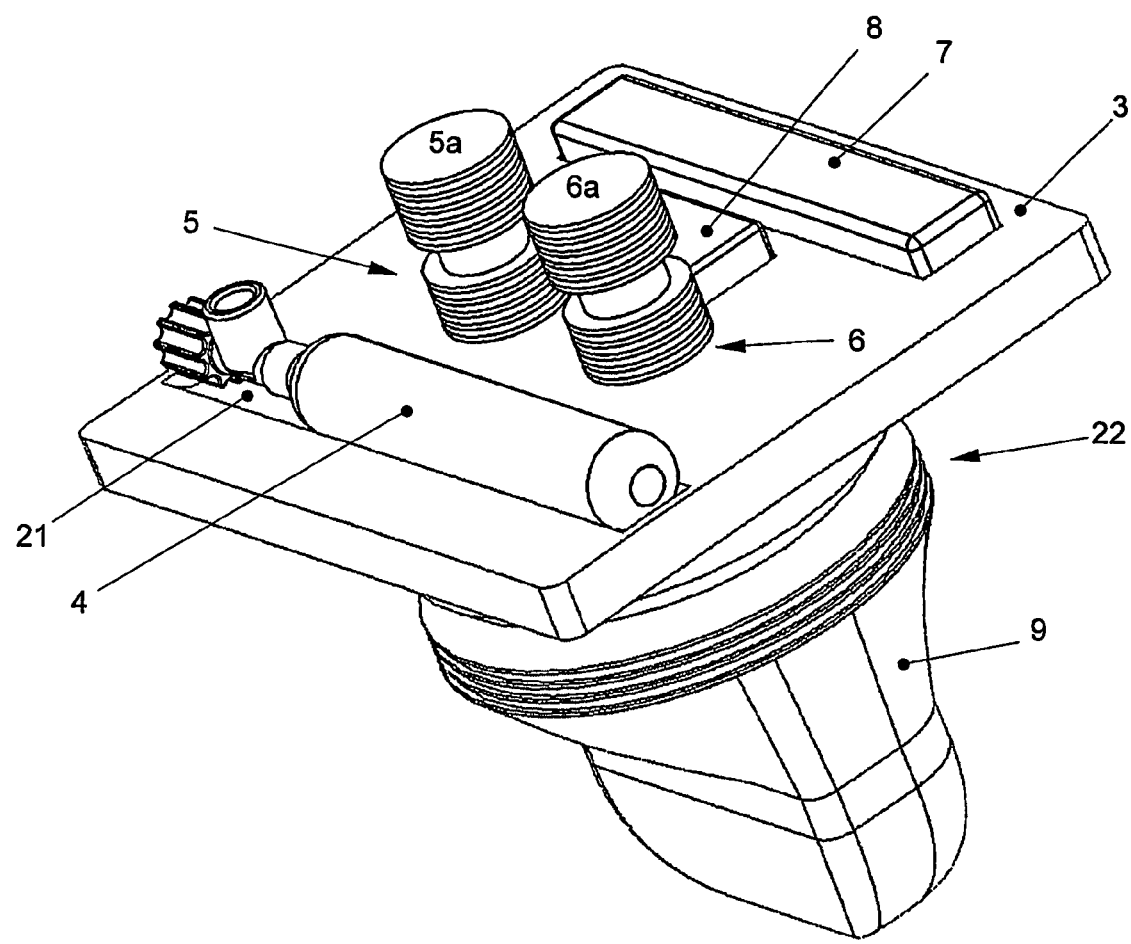
Figure 5:
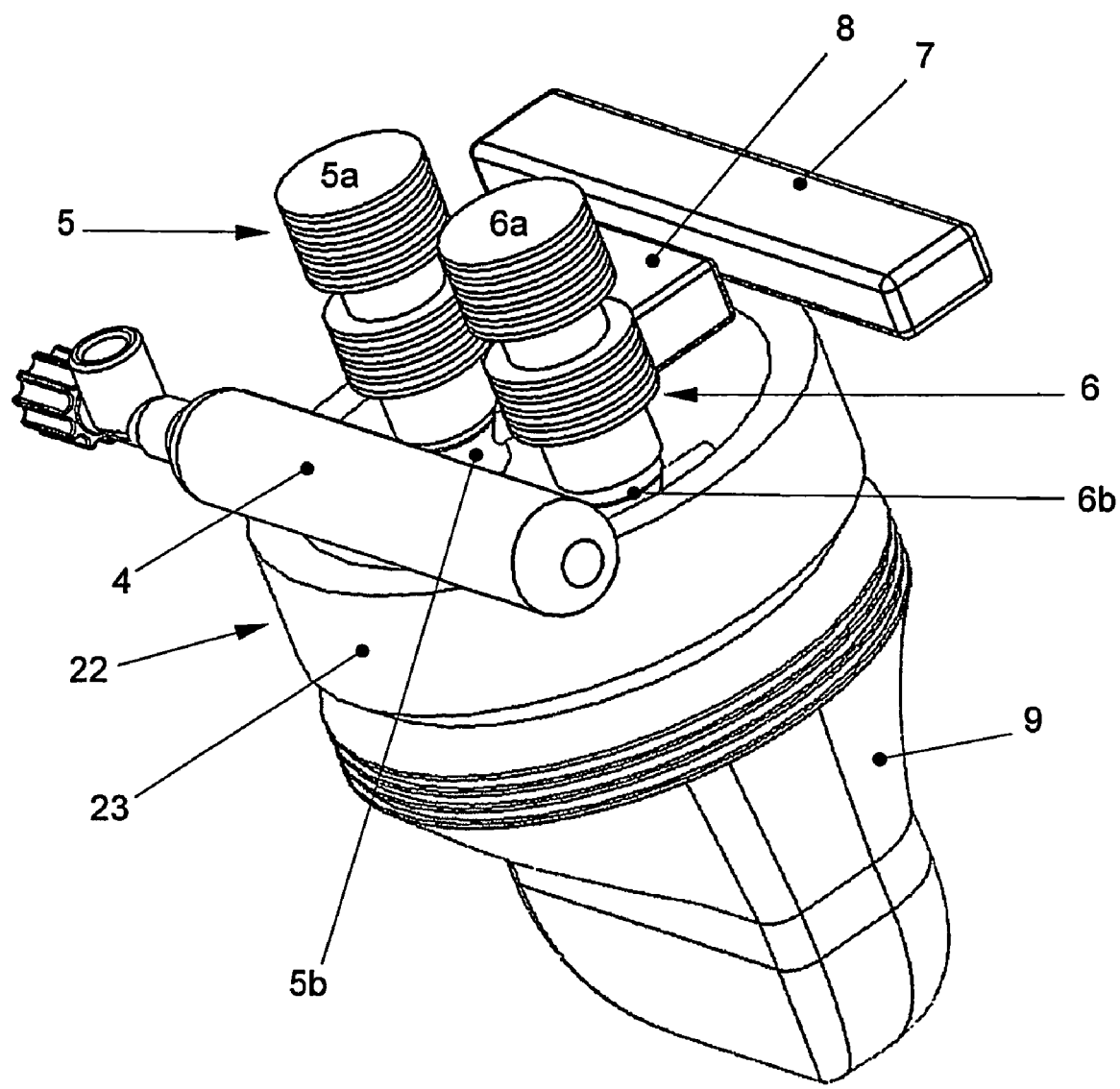
Figure 6:
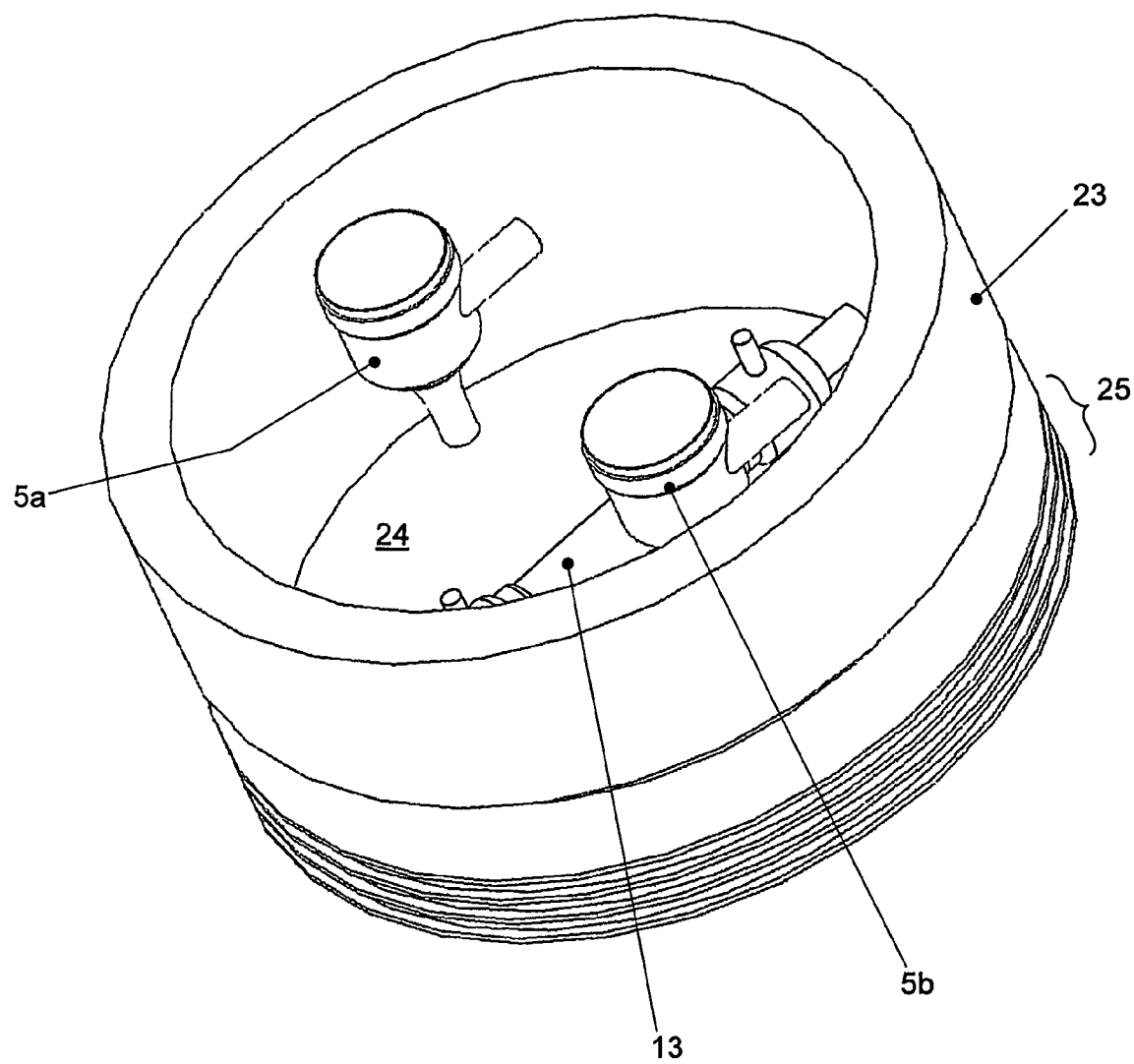
Figure 7:
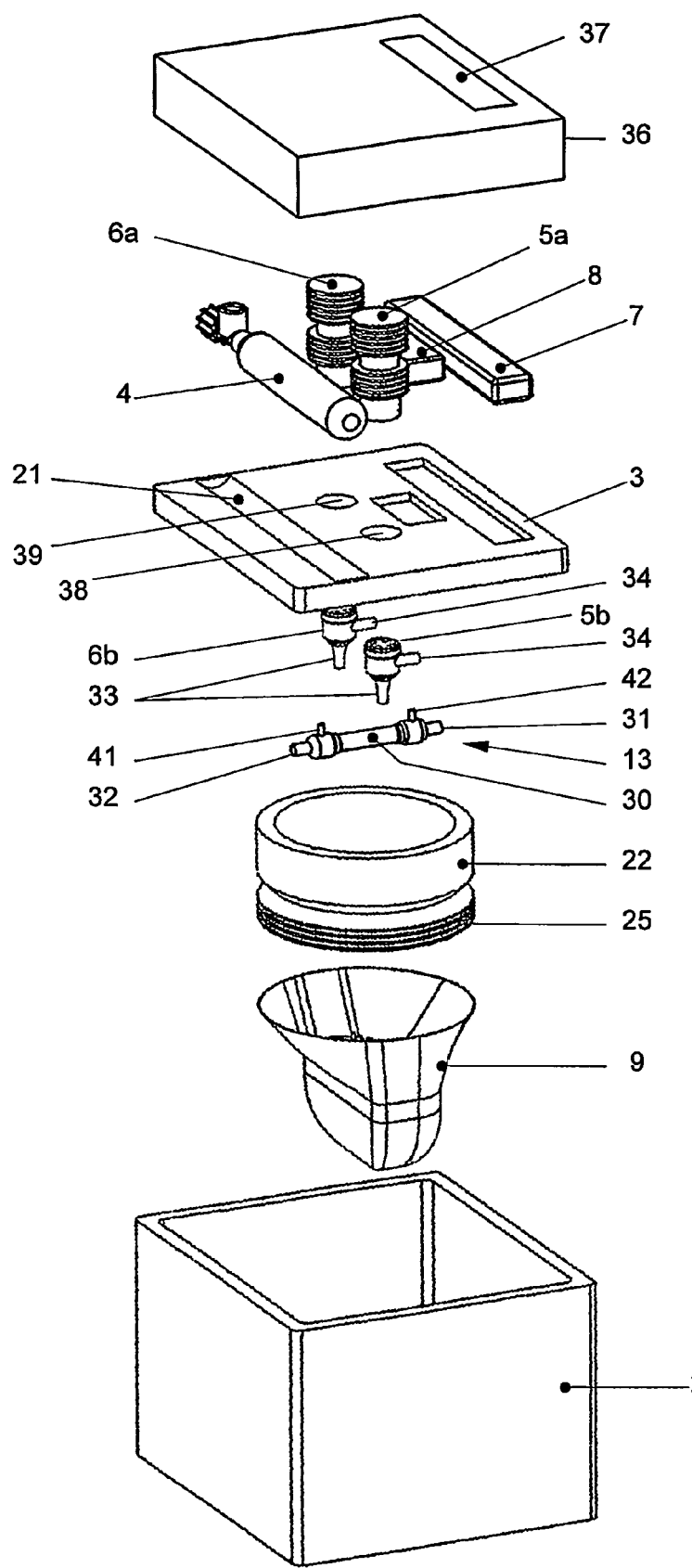

FIG. 4 diagrammatically shows, in perspective view, the lid of the apparatus of FIG. 1 with the parts of the preservation apparatus fastened thereto;

FIG. 5 shows a similar view to FIG. 5 but without the lid;

FIG. 6 diagrammatically shows, in perspective view, a connector of a preservation apparatus according to the invention; and FIG. 7 diagrammatically shows, in perspective view, the preservation apparatus of FIG. 1 in exploded view.

FIG. 1 diagrammatically shows, in perspective view, an example of a preservation apparatus 1 according to the invention. The apparatus shown comprises a cooling box 2 with a lid 3 drawn in the closing position in FIG. 1. On and in the lid 3, a number of components of the apparatus has been mounted, such as an oxygen container in the form of an oxygen cylinder 4, two small perfusion pumps 5,6 and modules 7,8 with control electronics, a power supply, etc. The power supply preferably comprises at least one battery, but may also comprise means such as for instance a transformer, a rectifier, a DC-DC converter etc., which are arranged to be able to offer electric energy in the suitable form, optionally from the electricity grid, to the control electronics and the pumps etc.

Figure 2:
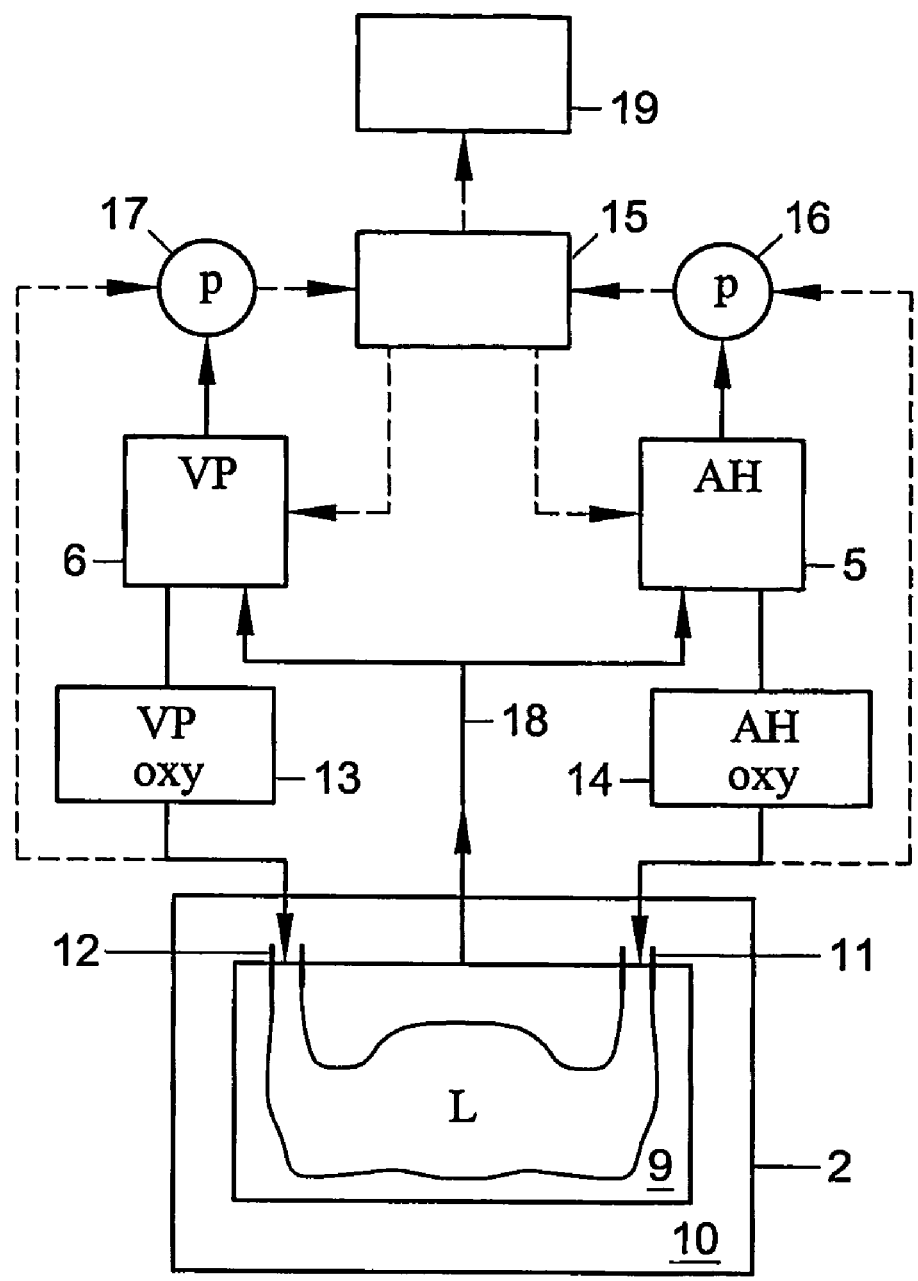
FIG. 2 shows a block diagram of an example of a portable preservation apparatus according to the invention.

FIG. 2 shows a block diagram of an example of a portable preservation apparatus according to the invention. In an organ chamber 10 formed in the cooling box 2, an organ L to be transplanted is present during use. This specification focuses on a liver to be transplanted, but the portable preservation apparatus according to the invention is also suitable for other organs such as for instance a kidney. During the donor operation, the liver is placed in a plastic bag 9 filled with preservative fluid. This bag has been placed in a second bag filled with physiological salt to prevent freezing damage. For safety reasons, usually a third bag is provided around the second bag. The thus packaged liver is placed in the organ chamber 10. During the donor operation, the portal vein (vena portae) and the arteria hepatica of the liver are provided with cannulas which are, in this example, each connected with the pumps 5,6 of FIG. 1 via an oxygenator 13,14. The hepatic vein ends in the bag 9 from which the pumps 5,6 suck in the perfusion fluid via one or more pipes 18 so that it can be recirculated. In FIG. 2, the pump 5 connected either directly or via a connecting tube 11 with the cannula of the arteria hepatica is designated by AH and the pump 6 connected either directly or via a connecting tube 12 with the vena portae is designated by VP. The pump 6 is connected with the vena portae via an oxygenator 13 (VP oxy). If desired, the pump 5 can also be connected either directly or via a second oxygenator (AH oxy), designated by 14, with the arteria hepatica. The pumps are preferably designed such that, selectively, either a continuous working mode or a pulsatile working mode is possible, so that, physiologically optimal perfusion conditions can be achieved. The connections which would be required for a different organ depend on the specific organ. For a kidney, for instance, only one connection with only one pump to the organ is required.

FIG. 2 also shows a control device 15, which controls the pumps 5 and 6 in response to the pressure P detected by means of pressure sensors 16,17 after the VP oxygenator 13, and after the pump 5, or, if present, the second oxygenator 14. The control device 15 is also connected with a microprocessor or a minicomputer, for instance a so-called palmtop computer 19, which is provided with a display screen and which is arranged to display relevant information, such as pressure in the cannulas, flow velocity and/or flow rate, temperature, time, alarm condition etc.

The display screen, any operating buttons or switches, indicator lamps and the like may, if desired, have been provided in a cover placed on the lid, which is diagrammatically shown in FIG. 7, designated by 36. Such a cover may of course also have a window 37 and/or flaps, behind which a display screen, buttons and the like are found.

Figure 3:
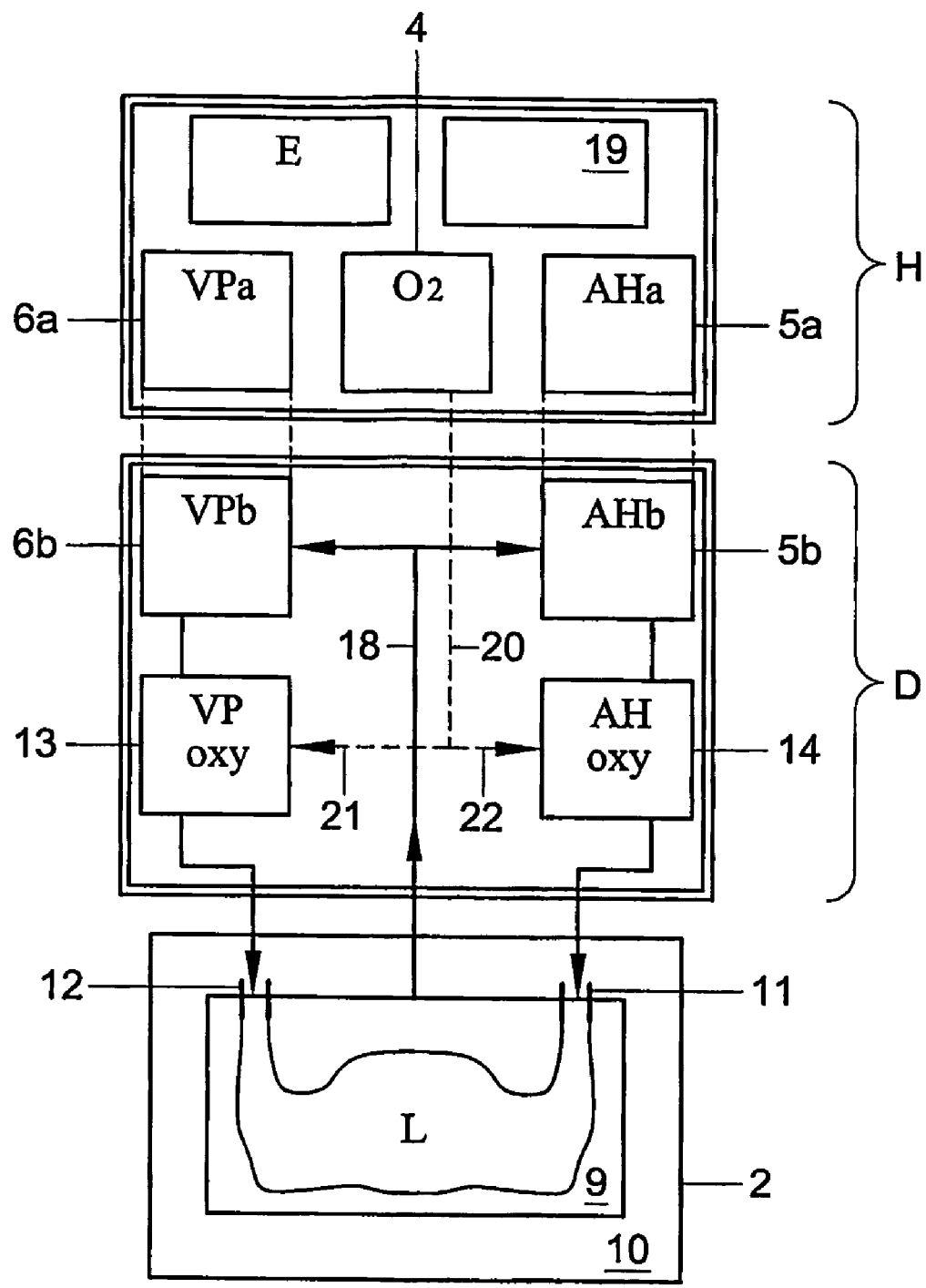
FIG. 3 shows a similar diagram to FIG. 2, in which the single-use and multiple-use parts, respectively, are shown.

FIG. 3 shows a similar diagram to FIG. 2, in which the single-use parts are designated by D and the parts which are reusable after use by H.

The reusable parts comprise the driving motors 5a (AHa) and 6a (VPa) of the pumps 5 and 6, respectively, for the arteria hepatica and the vena portae, respectively. The reusable parts further comprise the electronics E, the minicomputer 19 or the like and the oxygen cylinder 4, which is, via pipes 20,21, 22, connected with the oxygenator VP oxy and, if present, with the oxygenator AH oxy.

The single-use parts D comprise the parts of the pumps 5 and 6 which come into contact with the perfusion fluid. These are the parts 5b (AHb) and 6b (VPb) of the pumps. The oxygenator 13 for the vena portae and, if present, the oxygenator 14 for the arteria hepatica are also used only once. The same holds true for the pipes 18 between the organ bag 9 and the pump parts 5,6.

FIG. 4 diagrammatically shows the lid 3 of the cooling box 2 with the parts fastened to the lid and FIG. 5 shows these parts without the lid 3. As FIG. 4 shows, an oxygen cylinder 4 has been mounted on the lid 3. In this example, the oxygen cylinder is located in a recess 21 in the lid. The pipe(s) connected with the oxygen container which lead to the oxygenator(s) are not shown. On the lid, further, the reusable parts 5a and 6a of the pumps 5 and 6 have been mounted. Under the lid, a connector 22 has been mounted. The connector is detachably connected with the lid via a snap connection, a bayonet catch, a magnetic connection or the like. In the example shown, the connector has the shape of a short cylinder 23 closed at one end, as FIG. 6 shows best. The closed side or bottom of the connector faces the organ chamber. The bottom 24 is provided with passages and/or connecting pieces 11,12 for the cannulas and for the pipes coming from the oxygenator(s) and for the suction pipe(s) 18 of the pumps 5 and 6. In the connector, so-called disposable pump heads 5b, 6b, intended for single use and the oxygenator(s) 13, 14 are mounted. In the example of FIG. 6, only one oxygenator 13 is used for the vena portae. In use, under the connector, an organ bag 9 or a system of bags, as described hereinabove, has been fastened. In one of the manners known for this purpose, the organ bag 9 has been fixed on the connector 22, for instance with a so-called purse-string closure. Around this, an extra fastening, for instance a so-called tie-wrap, may be used. In the example shown, for obtaining a good closure, the connector is provided with a number of circular circumferential grooves 24 or ribs, respectively. A suitable organ bag is the Vi-Drape organ bag of Medical Concepts Development in St. Paul Minn. (USA). In a test arrangement, further, for the vena portae and the arteria hepatica, cannulas were used of Sherwood Medical in Tullamore (Ireland) and pumps with a motor of the type Deltastream DP2 and a pump head for single use of MEDOS Medizintechnik AG, in Stolberg (Germany).

The pump motor can be snapped on the pump head via an opening in the lid 3, for instance by using a magnetic coupling or the like. Alternatively, other commercially available miniature pumps, such as for instance the impella pump of Impella Cardiotechnik AG, in Aken (Germany), can be used.

All parts of the preservation apparatus which come into contact with the perfusion fluid have been mounted in the connector, with the exception of the organ bag. Thus, the connector with the parts connected thereto can be treated as a single-use replacement part.

The oxygenator 13 partly visible in FIG. 6 and wholly visible in FIG. 7 comprises a tubular body 30 filled with fibers with, at one end, an inlet connection 31 connected with the pump 6 and, at the other end, an outlet connection 32, connected with the cannula 12 during use. Via the vertical (in the drawing) connection pipes 41, 42, oxygen is passed through the tubular body from the oxygen cylinder 4 in counterflow. Optionally, the oxygen supply may take place intermittently.

In this example, the pump heads 5b and 6b have an axial suction inlet 33, which is in connection with the organ chamber, and a radial discharge outlet 34, which is connected with the inlet connection 31 of the oxygenator 13 on the vena portae side. On the arteria hepatica side, the discharge outlet 34 of the pump head 6b can be connected either directly with the corresponding cannula 11 or with the inlet connection 31 of the oxygenator 14, depending on the fact whether a second oxygenator 14 is used.

FIG. 7 diagrammatically shows, in perspective, in exploded view, a portable preservation apparatus according to the invention. Also in FIG. 7, only one oxygenator 13 is shown but, as already noted, two oxygenators can be used. FIG. 7 also shows the openings 38, 39 in the lid 3, which make it possible to fasten the pump motors 5a, 6a on the pump heads 5b, 6b such that at least one perfusion pump is mounted at least partly in lid. Further, receiving cavities 39, 40 are shown for modules 7 and 9.

It is noted that, after the foregoing, various variants are obvious to a skilled person. As already noted before, a portable preservation apparatus according to the invention is also suitable for transporting and perfusing different organs than a liver. In that case, the number of cannulas, pumps and oxygenators needs to be adjusted.

Further, the connector may also have a different cross-sectional shape than the circular shape shown, for instance an oval shape. Also, in a practical embodiment, the apparatus will be provided with one or more handgrips, carrying handles, running wheels and the like, which are not shown in the drawings.

For obtaining the desired cooling, the cooling box may be filled with ice and/or passive cooling elements and/or provided with a cooling device running on electricity or gas. It is further noted that a number of the parts mounted in or to the lid according to the foregoing specification may also be mounted in one or more fixed walls, or in a detachable part of a fixed wall. It is finally noted that the cooling box may also be used without cooling as a stove for, for instance, storing an organ at 37° C.

The invention claimed is:

1. A portable preservation apparatus of the cold storage type for a donor organ, comprising:
    (a) a cooling box having a lid, said cooling box having an interior surface;
    (b) a package for containing a donor organ in preservation fluid;
    (c) at least one perfusion pump mounted at least partly in the lid;
    (d) a connector;
    (e) at least one oxygenator for oxygenating preservation fluid;
    (f) an oxygen container for supplying oxygen to the oxygenator;
    (g) one or more electronic modules for controlling the perfusion pump; and
    (h) a power supply module for supplying power to the apparatus;
wherein the cooling box has an organ chamber for receiving the package, the lid of the cooling box having a side which operatively faces the organ chamber, the connector being detachably connected to the lid on the side of the lid which operatively faces the organ chamber, the package being detachably and sealingly connected to the connector and extending from the connector in the organ chamber, the connector being provided with one or more passages to permit preservation fluid in the package to be pumped by the perfusion pump, the connector and the package being configured and sealed so that preservation fluid in the package will not contact (1) the interior surface of the cooling box and (2) the lid.

2. A portable preservation apparatus according to claim 1, wherein the connector has the form of a container open on one side, and is provided with fastening elements which can cooperate with fastening elements provided to the lid for fastening the connector to the lid in such a detachable manner that the open side of the container faces the lid, while the one or more passages are located in an otherwise closed wall facing the organ chamber.

3. A portable preservation apparatus according to claim 1, wherein the at least one oxygenator, at least the part of the at least one perfusion pump coming into contact with the preservative fluid and the corresponding fluid pipes are mounted in the connector, so that, together with the said at least one oxygenator, said at least part of the at least one perfusion pump coming into contact with the preservative fluid and said corresponding fluid pipes, the connector forms a single-use replacement part.

4. A portable preservation apparatus according to claim 1, wherein the at least one perfusion pump is a pump with a detachable driving motor, which driving motor is, in mounted condition, located on the side of the lid for the cooling box facing away from the connector and is detachably connected with the remaining part of the pump via an opening in the lid for the cooling box, which remaining part of the pump is mounted in the connector.

5. A portable preservation apparatus according to claim 1, wherein the lid for the cooling box is provided with at least one of the one or more electronic modules and/or the oxygen container.

6. A portable preservation apparatus according to claim 1, wherein the one or more electronic modules comprises a minicomputer for controlling the pumping action of the at least one perfusion pump and the displaying of relevant data.

7. A portable preservation apparatus according to claim 6, further including a cover on the lid, which cover at least partly forms a window of a display screen of the minicomputer.

8. A portable preservation apparatus according to claim 1, wherein, on the outside of the connector, near a wall of the connector facing the organ chamber, the connector is provided with a number of circumferential grooves and/or ribs for fastening an organ bag.

9. A portable preservation apparatus according to claim 1, wherein the connector has the form of a container open on one side, said open side facing the lid, said perfusion pump comprising a pump motor and a pump head, said pump head and said at least one oxygenator being mounted in said container.

10. A portable preservation apparatus according to claim 1, wherein said perfusion pump comprises a pump motor and a pump head, said apparatus being configured so that preservation fluid in the package will contact said pump head but will not contact said pump motor.

* * * * *

UNITED STATES PATENT AND TRADEMARK OFFICE
CERTIFICATE OF CORRECTION

| | | |
|---|---|---|
| PATENT NO. | : 7,811,808 B2 | Page 1 of 1 |
| APPLICATION NO. | : 10/566415 | |
| DATED | : October 12, 2010 | |
| INVENTOR(S) | : Arjan van der Plaats | |

It is certified that error appears in the above-identified patent and that said Letters Patent is hereby corrected as shown below:

Title page, item [75] inventor, delete the name of the sixth inventor

"Hendrik Gerrit Derk Leuvelink" and insert therefor

-- Hendrik Gerrit Derk Leuvenink --.

Signed and Sealed this
Fifteenth Day of February, 2011

David J. Kappos
*Director of the United States Patent and Trademark Office*